Aug. 6, 1968 C. F. ZAIGER Plant Pat. 2,825
NECTARINE TREE
Filed Sept. 21, 1966
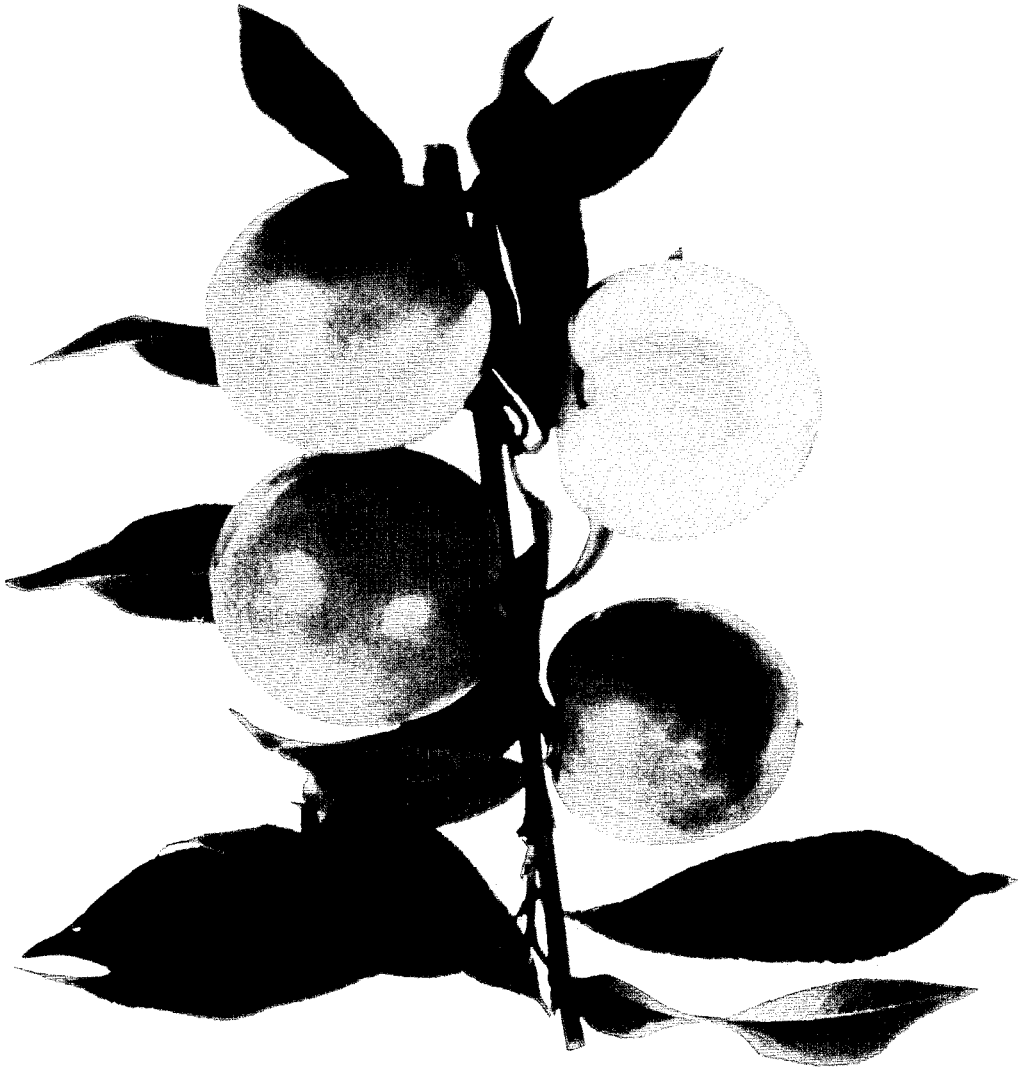
INVENTOR
C. Floyd Zaiger United States Patent Office Plant Pat. 2,825
Patented Aug. 6, 1968

2,825
NECTARINE TREE

Chris Floyd Zaiger, 537 Rosemore Ave.,
Modesto, Calif. 95351

Filed Sept. 21, 1966, Ser. No. 581,426
1 Claim. (Cl. Plt.—41)

My invention relates to a new and distinct variety of nectarine tree which bears yellow-fleshed fruit characterized as to novelty by ripening earlier, having higher red color, greater firmness than the present commercial varieties; the ripening period being approximately fourteen days earlier than the Grand River nectarine (United States Plant Patent No. 1,248) and the Merrill Sunrise nectarine (United States Plant Patent No. 1,256). The new variety is also characterized by having fruit that colors two to three weeks before ripening, having larger, smoother, highly colored fruit than other early varieties.

The new variety of nectarine tree was originated in my experimental orchard at Modesto, Calif. It was selected from a number of seedlings, the varietal type of which was unknown. Variety most resembles the nectarine of Early Sun Grand (Plant Patent 1,420) as to color, firmness, shape and size with the exception of being earlier maturing.

The present variety was asexually propagated by grafting and budding, as performed at Modesto, Calif., shows that said characteristics come true to form and are established and transmitted through succeeding propagation.

The accompanying photographs show typical specimens of the foliage and fruit of my new variety, with upper and lower surfaces of the foliage being illustrated and exterior and a sectional view of the fruit being shown. The illustrations were taken shortly after being picked at maturity (shipping ripe), and the colors are as nearly true as reasonably possible in a color representation of this type.

The following is a detailed description of the foliage and fruit of my new variety, as based upon observations of specimens grown at Modesto, Calif., with color terminology in accordance with Reinhold Color Atlas by A. Kornerup and J. H. Wanacher.

Date of first and last picking: Generally ripens in late May; although over prolonged observations, dates of first ripening varied from May 23 to June 1 with last picking from June 2 to June 10.

Tree:
- *Size.*—Large.
- *Vigor.*—Vigorous.
- *Form.*—Spreading.
- *Production.*—Very productive.
- *Bearing.*—Regular.

Trunk: Size—medium to stocky.

Branches: Size—stocky to medium.

Leaves:
- *Size.*—Large to medium. Length—average, five and one-half inches. Width—average, one and one-half inches.
- *Texture.*—Smooth.
- *Margin.*—Crenate.
- *Petiole.*—Medium length.
- *Glands.*—Usually two or more, medium size, reniform.
- *Color.*—Upper surface, deep green, Plate No. 28E8. Lower surface, grayish-green, Plate No. 29D5.

Flower buds: Medium size, medium length, plump, free, pubscent.

Flowers:
- *Size.*—Large to medium.
- *Blooming period.*—Date of first bloom—Mar. 4, 1965. Date of full bloom—Mar. 12, 1965.
- *Pollen.*—Present.
- *Color.*—Pink.

Fruit:
- *Maturity.*—June 6, 1965. Date of first picking—May 25, 1965. Date of last picking—June 6, 1965.
- *Size.*—Medium, uniform. Average axial diameter—two and one-half inches. Average diameter transverse in suture plane—2¼". Average diameter at right angles to suture plane—2¼".
- *Form.*—Symmetrical; narrowly ovid.
- *Suture.*—Shallow, extends from base to apex.
- *Ventral surface.*—Rounded slightly; lips mostly equal.
- *Cavity.*—Rounded, average depth, ⅜"; average breadth, 1".
- *Base.*—Rounded.
- *Apex.*—Short.
- *Pistil point.*—Apical.

Skin:
- *Thickness.*—Medium.
- *Texture.*—Tough to medium, tenacious to flesh, smooth.
- *Tendency to crack.*—None.
- *Down.*—Wanting.
- *Color.*—Red, Plate No. 10B8, to a deeper red, Plate No. 11C8.

Flesh:
- *Amygadalin.*—Moderate.
- *Juice.*—Moderate.
- *Texture.*—Firm, crisp, meaty.
- *Fibers.*—Few, fine, tender.
- *Ripens.*—Fairly evenly, but slightly earlier at the apex.
- *Flavor.*—Subacid.
- *Aroma.*—Very little.
- *Eating quality.*—Good.
- *Color.*—Yellowish-orange, Plate No. 4A7, to golden yellow, Plate No. 5A7.

Stone:
- *Type.*—Cling; adheres to flesh over entire surface.
- *Fibers.*—Short.
- *Size.*—Medium, average length 1½ inches; average breadth 1 inch; average thickness ⅝ inch.
- *Form.*—Mostly obovate, tip acuminate.
- *Base.*—Mostly straight.
- *Hilum.*—Oval.
- *Apex.*—Acuminate.
- *Sides.*—Mostly equal.
- *Surface.*—Furrowed throughout with heavy deep furrows toward point and dorsal side; ridged throughout pistil.
- *Ridges.*—Rounded; interrupted.
- *Pits.*—Elongated.
- *Dorsal edge.*—Narrow.
- *Ventral edge.*—Thin, without wing.
- *Tendency to split.*—Slight.
- *Color.*—Light brown, Plate No. 8D6.

Use: Market, dessert.

Shipping and keeping quality: Good.

The tree and its fruit herein described may vary in slight detail due to climatic and soil conditions under which the variety may be grown. The description is that of the variety produced under ecological conditions prevailing at Modesto, Calif., and the characteristics are found to hold true in asexual reproduction of the variety.

The following is claimed:

1. A new and distinct variety of nectarine tree, as illustrated and described, characterized by medium to large size and heavy production; its bearing of firm, yellow fleshed, intensely red nectarines and which ripen approximately fourteen days earlier than the Grand River nectarine (United States Plant Patent No. 1,248) and the Merrill Sunrise nectarine (United States Plant Patent No. 1,256).

No references cited.

ROBERT E. BAGWILL, *Primary Examiner.*